United States Patent [19]

Burk et al.

[11] 4,163,798

[45] Aug. 7, 1979

[54] STABILIZED AQUEOUS AMIDE ANTIMICROBIAL COMPOSITION

[75] Inventors: George A. Burk, Bay City; Charles A. Wilson; Charles E. Reineke, both of Midland, all of Mich.

[73] Assignee: The Dow Chemical Company, Midland, Mich.

[21] Appl. No.: 860,642

[22] Filed: Dec. 14, 1977

[51] Int. Cl.$^2$ ............................................. A01N 9/20
[52] U.S. Cl. .................................. 424/304; 424/267; 424/320; 424/333; 424/334
[58] Field of Search ............... 424/304, 334, 333, 320, 424/267

[56] References Cited

U.S. PATENT DOCUMENTS

| | | | |
|---|---|---|---|
| 3,350,265 | 10/1967 | Rubinstein et al. | 424/334 |
| 3,689,660 | 9/1972 | Burk et al. | 424/304 |
| 3,751,444 | 8/1973 | Solem et al. | 260/465.4 |
| 4,022,605 | 5/1977 | Konya et al. | 424/304 |

*Primary Examiner*—V. D. Turner
*Attorney, Agent, or Firm*—James B. Guffey

[57] ABSTRACT

Aqueous antimicrobial compositions which comprise a halogenated amide antimicrobial, such as 2,2-dibromonitrilopropionamide, a water miscible organic solvent such as a straight chain polyalkylene glycol (e.g., polyethylene glycol 200) or an ether thereof (e.g., a mono- or di- lower alkyl and/or phenyl ether) and water are stabilized against decomposition of the halogenated amide antimicrobial by the addition of an aldehyde stabilizer, such as formaldehyde, paraformaldehyde, N-formyl piperidine, vanillin, etc. The compositions so stabilized exhibit reduced rates of decomposition of the halogenated amide antimicrobial relative to the corresponding non-stabilized aqueous compositions.

19 Claims, No Drawings

4,163,798

STABILIZED AQUEOUS AMIDE ANTIMICROBIAL COMPOSITION

BACKGROUND OF THE INVENTION

This invention relates to stabilized aqueous antimicrobial compositions which comprise a halogenated amide as the active (i.e., antimicrobial) ingredient and to processes for their preparation.

Halogenated amides such as 2,2-dibromonitrilopropionamide are useful as antimicrobials in various applications. See, for example, Nolan et al., U.S. Pat. No. 2,419,888; Schmidt et al., U.S. Pat. No. 3,493,658; and CIBA S.A. Belgian Pat. No. 668,336. Certain halogenated amides are useful in the finishing of textiles, as taught by Chance et al., U.S. Pat. Nos. 3,350,164 and 3,403,174. Others are useful as slimicides in aqueous systems such as paper pulp and cooling towers and as sterilizing agents for drycleaning fluids. See, for example, Wolf, U.S. Pat. No. 3,647,610; Wolf, U.S. Pat. No. 3,649,166; Wolf et al., "2,2-Dibromo-3-Nitrilopropionamide, A Compound with Slimicidal Activity", *Applied Microbiology*, Vol. 24, No. 4, pp. 581–584 (1972); and Moyle et al., U.S. Pat. No. 3,928,575.

In the storage, shipment and use of such antimicrobial agents, it is often desirable to employ the antimicrobial agent in the form of a liquid concentrate composition wherein the halogenated amide antimicrobial is dissolved in a mixture of an organic solvent and water. However, the presence of water in such compositions often accelerate decomposition of the halogenated amide anti-microbial. See, for example, U.S. Pat. No. 3,689,660 and "Rates and Products of Decomposition of 2,2-Dibromo-3-Nitrilopropionamide", Exner et al., *J. Agr. Food Chem.*, Vol. 21, No. 5, pp. 838–842 (1973). Accordingly, in order to obtain adequate stability for many purposes, it has heretofore been necessary to resort to essentially anhydrous liquid concentrate compositions and it has therefore been necessary to essentially exclude water from the ingredients used in the preparation thereof.

Consequently, it is desirable to provide a means of reducing the adverse impact of water upon the aforementioned liquid concentrate compositions and to thereby provide (a) aqueous halogenated amide antimicrobial compositions having improved stability and (b) simplified, economical processes for the preparation of stable liquid concentrate compositions.

SUMMARY OF THE INVENTION

It has now been found that the rate of decomposition of the halogenated amide antimicrobial in the aforementioned aqueous liquid concentrate compositions is substantially reduced by the addition of an aldehyde stabilizer. Thus, in one aspect the instant invention is a stabilized aqueous antimicrobial composition, which comprises: (1) a water miscible organic solvent; (2) water; (3) a halogenated amide antimicrobial; and (4) a stabilizing amount of an aldehyde stabilizer. Typically, such composition has a pH of from about 2 to about 5, preferably from about 3 to about 4.

In another aspect the instant invention is a process for preparing an aqueous halogenated amide antimicrobial composition wherein the aqueous component of such composition comprises the aqueous reaction medium in which the halogenated amide antimicrobial was prepared. Such process comprises the steps of:

(a) preparing the halogenated amide antimicrobial by the acid catalyzed reaction of a non-halogenated amide with halogen in aqueous solution;

(b) dissolving the resulting aqueous reaction mixture in a water miscible organic solvent; and (c) adding to the reaction mixture, or to the water miscible organic solvent solution thereof, a stabilizing amount of an aldehyde stabilizer.

Typically, the aforementioned process also involves a pH adjustment step such that the composition resulting from such process has a pH of from about 2 to about 5, preferably from about 3 to about 4.

As used herein, the term "water miscible" means that the organic solvent is soluble in water (i.e., mixes or blends uniformly with water) at least to the degree required to achieve the desired solvent to water ratio in the aqueous composition and preferably the organic solvent is soluble in water in all proportions.

The terms "antimicrobial compound" and "halogenated amide antimicrobial" are used interchangeably herein and refer to halogenated amides which function as biocides (i.e., compounds which inhibit the growth of, or kills, microorganisms such as bacteria, molds, slimes, fungi, etc.).

The term "stabilizing amount" as employed herein refers to an amount of stabilizer sufficient to measurably reduce the decomposition rate of the halogenated amide antimicrobial in the aqueous antimicrobial composition. The aforementioned reduction in the decomposition rate of the halogenated amide antimicrobial is, of course, relative to the decomposition rate encountered with a corresponding aqueous antimicrobial composition in the absence of the stabilizer under the same test conditions. Such reduction is deemed to be "measurable" if it is detectible (and reproducible) by the iodometric test method which is described hereinafter in conjunction with the working examples.

The aqueous antimicrobial compositions of the invention are useful as slimicides in aqueous systems such as paper pulping processes and cooling towers and as sterilizing agents for drycleaning fluids. Such compositions exhibit improved stability toward decomposition of the halogenated amide antimicrobial for extended periods under a wide variety of storage, packaging and handling conditions. They are easily handled and can be employed in the above applications pursuant to conventional techniques such as those described in U.S. Pat. No. 3,689,660.

The indicated process for preparing the aqueous antimicrobial composition is advantageous in that suitably stable compositions can be prepared without separation of the halogenated amide antimicrobial from the aqueous medium in which it was prepared.

DETAILED DESCRIPTION OF THE INVENTION

Halogenated amide antimicrobials employed in the practice of this invention are alpha-haloamides; that is, compounds which contain an amide functionality (i.e., a moiety of the formula $-C(O)-N<$) and which have at least one halogen atom on a carbon atom located adjacent to (i.e., in the alpha position relative to) the carbonyl group (i.e., the $-C(O)-$ group) of such amide functionality. Advantageously, such halogenated amide antimicrobials are halogenated nitrilopropionamides or halogenated malonic diamides having the formula:

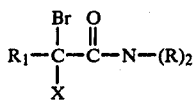

wherein:

X is hydrogen, halogen or a cyano radical, i.e., —C≡N, (preferably hydrogen, chlorine or bromine);

each R group is independently hydrogen, a monovalent "saturated hydrocarbon radical" or an inertly substituted monovalent "saturated hydrocarbon radical" or the two R groups are, jointly, a divalent "saturated hydrocarbon radical", or an inertly substituted divalent "saturated hydrocarbon radical", which, taken with the adjacent nitrogen atom, forms a heterocyclic ring having from 4 to about 10 ring members; and $R_1$ is a cyano radical (i.e., —C≡N) or an amido radical having the formula:

wherein R is as hereinbefore defined. (Preferably, $R_1$ is a cyano radical.)

As used herein, the term "saturated hydrocarbon radical" refers to a hydrocarbon radical which is free from aliphatic carbon to carbon unsaturation. Thus, such term includes radicals such as alkyl, cycloalkyl, aryl, alkylaryl, arylalkyl, cycloalkylaryl, etc., and excludes radicals such as alkenyl, cycloalkenyl, alkynyl and the like.

As used herein, the term "inertly substituted saturated hydrocarbon radical" refers to a "saturated hydrocarbon radical" having one or more chain linkage or substituent which is "inert" in the sense that such chain linkage or substituent does not readily react with the ingredients of the aqueous antimicrobial composition. Suitable inertly substituted saturated hydrocarbon radicals thus include, for example, haloalkyl, haloaryl, halocycloalkyl, aminoalkyl, aminoaryl, aminocycloalkyl, hydroxyalkyl, hydroxyaryl, hydroxycycloalkyl, cyanoalkyl, cyanoaryl, cyanocycloalkyl, and the like.

The aforementioned halogenated amide antimicrobials of the formula I thus include brominated nitrilopropionamides (i.e., compounds of the formula I wherein $R_1$ is a cyano radical), such as 2-bromo-3-nitrilopropionamide, 2-bromo-2,3-dinitrilopropionamide, 2,2-dibromo-3-nitrilopropionamide, N-(n-butyl)-2-bromo-3-nitrilopropionamide; N,N-dimethyl-2,2-dibromo-3-nitrilopropionamide, 2-chloro-2-bromo-3-nitrilopropionamide, N-(n-propyl)-2-iodo-2-bromo-3-nitrilopropionamide, N-methyl-N-ethyl-2-fluoro-2-bromo-3-nitrilopropionamide, N-phenyl-2-cyano-2-bromo-3-nitrilopropionamide, N-cyclohexyl-2,2-dibromo-3-nitrilopropionamide, N-benzyl-2-bromo-3-nitrilopropionamide, N-(2,2-dibromo-3-nitrilopropionoyl)-piperidine and the like.

The aforementioned halogenated amide antimicrobials of the formula I also include mino- and di-bromomalonic diamides (i.e., compounds of the formula I wherein $R_1$ is an amino radical as hereinbefore described), such as 2-bromomalonic diamide, 2,2-dibromomalonic diamide, N-methyl-N'-ethyl-2-bromomalonic diamide, N-phenyl-2-iodo-2-bromomalonic diamide, and the like.

Among the aforementioned halogenated amide antimicrobials, those wherein, in the formula I, $R_1$ is a cyano radical, X is hydrogen, chlorine or bromine and each R is independently hydrogen, lower alkyl (e.g., an alkyl group of from 1 to about 6 carbon atoms) or phenyl are preferred, especially those of the formula I wherein each R independently is hydrogen or methyl and X is hydrogen or bromine. Such halogenated amide anti-microbials include 2-bromo-3-nitrilopropionamide, 2,2-dibromo-3-nitrilopropionamide, N-methyl-2-bromo-3-nitrilopropionamide, N-phenyl-2-bromo-2-chloro-3-nitrilopropionamide, N-methyl-2,2-dibromo-3-nitrilo-propionamide, N,N-dimethyl-2-bromo-3-nitrilopropionamide, N,N-diethyl-2,2-dibromo-3-nitrilopropionamide, and N,N-dimethyl-2,2-dibromo-3-nitrilopropionamide.

Also of particular interest are the dibrominated nitrilopropionamides (i.e., the halogenated amide antimicrobials of the formula I wherein X is bromine and $R_1$ is cyano) wherein each R independently is hydrogen, lower alkyl or phenyl. Such compounds include 2,2-dibromo-3-nitrilopropionamide, N-(n-butyl)-2,2-dibromo-3-nitrilopropionamide, N,N-dimethyl-2,2-dibromo-3-nitrilopropionamide, N-phenyl-N-methyl-2,2-dibromo-3-nitrilopropionamide and the like; especially 2,2-dibromo-3-nitrilopropionamide.

The aqueous antimicrobial compositions of the invention normally contain from about 1 to about 25 percent by weight of the hereinbefore described halogenated amide antimicrobial based upon the total weight of the composition. However, the decomposition of the halogenated amide antimicrobials has been observed to be more pronounced when the aqueous compositions contain less than about 20 percent by weight of the antimicrobal on a total weight basis. Thus, stabilized aqueous antimicrobial compositions which, by virtue of the relatively more pronounced benefits of stabilization, are of particular interest comprise from about 1 to abou 15, preferably from about 1 to about 10, most preferably from about 1 to about 5, weight percent of the total composition.

In the composition of this invention, the aforementioned halogenated amide antimicrobial is dissolved in a mixture of water and a water miscible organic solvent. Suitable organic solvents include any water miscible organic solvent in which the halogenated amide antimicrobial is at least partially soluble. Preferably the organic solvent is one in which the halogenated amide antimicrobial is soluble at normal room temperature (i.e., from about 20° to about 25° C.) to the extent of at least about 5 parts by weight of the antimicrobial in about 95 parts by weight of the solvent. The most preferred water miscible organic solvents are those in which the antimicrobial is soluble to the extent of at least about 10 (especially at least about 20) parts by weight of the antimicrobial in about 80 parts by weight of the solvent at normal room temperatures (i.e., from about 20° to about 25° C.).

Advantageously, the organic solvent is a polyalkylene glycol or an ether thereof, especially a normally liquid straight chain polyalkylene glycol or a mono- or di-saturated hydrocarbyl ether thereof wherein the term "saturated hydrocarbyl" refers to a monovalent saturated hydrocarbon radical as is hereinbefore defined.

Generally, such polyalkylene glycols and polyalkylene glycol ethers have a weight average molecular weight (Mw) of from about 75 to about 1000. Such average molecular weights are hereinafter designated for the particular glycols involved by placing a numeral representing the weight average molecular weight after the glycol name.

Of particular interest in the practice of the invention are the polyalkylene glycols of the ethylene, trimethylene, or tetramethylene series and the mono- and di-lower (e.g., containing from 1 to about 6 carbon atoms) saturated hydrocarbyl ethers thereof. Examples of such particularly advantageous solvents include polyethylene glycols, trimethylene glycols, tetramethylene glycols and the mono- and di- lower saturated hydrocarbyl (e.g., lower alkyl, i.e., $C_1$ to about $C_6$ alkyl, and phenyl) ethers of such glycols.

Examples of the aforementioned polyalkylene glycols and ethers include 1,4-butanediol, triethylene glycol, polyethylene glycol 200, tetraethylene glycol, polyethylene glycol 400, diethylene glycol dimethyl ether, diethylene glycol phenyl ether, diethylene glycol ethyl phenyl ether, polytrimethylene glycol 200, diethylene glycol, triethylene glycol methyl ether and polyethylene glycol 600.

Preferably, the polyalkylene glycol or ether ingredient is a polyethylene glycol, or a mixture of polyethylene glycols, having Mw of from about 175 to about 250. Most preferably the polyalkylene glycol ingredient is polyethylene glycol 200.

The amount of the aforementioned water miscible organic solvent employed in the practice of the invention is not particularly critical. Advantageously, however, a sufficient amount is employed to prevent precipitation of the halogenated amide antimicrobial during shipping, storage and use of the aqueous antimicrobial composition. The amount of the organic solvent desirably employed will thus depend upon such factors as the solubility of the halogenated amide antimicrobial in the organic solvent, the desired concentration of the halogenated amide anti-microbial in the composition, and the like. However, as a general rule the organic solvent constitutes from about 5 to about 90, preferably from about 10 to about 80, more preferably from about 25 to about 75, most preferably from about 35 to about 70, percent by weight of the total antimicrobial composition.

As has been noted, any of the aforementioned water miscible organic solvents can be suitably employed in the practice of this invention to dissolve the aforementioned halogenated amide antimicrobial. However, it has been found (and such finding constitutes the subject matter of a commonly owned application by George A. Burk, Charles A. Wilson and Charles A. Reineke, filed even date herewith) that the aforementioned problem of halogenated amide decomposition under aqueous conditions is substantially more pronounced in the presence of salts of organic acids and/or glycols having a molecular weight of less than about 70 grams per mole; both of which, for example, are potentially common minor impurities in many commercially available unpurified polyalkylene glycols and ethers thereof. Thus, the benefits attributable to the herein disclosed stabilizers are relatively more pronounced in those stabilized aqueous antimicrobial compositions which employ organic solvents containing the aforementioned impurities or which contain such impurities from some other source.

The amount of water contained by the aqueous antimicrobial composition of the invention is likewise not particularly critical to the practice of the invention. However, as a general rule the compositions of the invention employ water in an amount of from about 5 to about 90, preferably from about 10 to about 85, more preferably from about 15 to about 70, most preferably from about 20 to about 60 weight percent based upon the weight of the total antimicrobial composition.

The aldehyde stabilizers employed in the practice of this invention are aldehydes or inertly substituted aldehydes wherein the term "inertly substituted" indicates that, in addition to the aldehyde functionality, i.e., —C(O)H, the stabilizer can also contain one or more chain linkage of oxygen, sulfur or nitrogen and/or one or more hydroxyl, cyano (i.e., —C≡N), or —NO$_2$ substituent.

Examples of the aforementioned aldehyde stabilizers include saturated aliphatic aldehydes, such as formaldehyde, paraformaldehyde, etc.; saturated alicyclic aldehydes such as N-formyl piperidine, etc.; and carbocyclic aromatic aldehydes such as 3-methoxy-4-hydroxybenzaldehyde, p-nitro-benzaldehyde, o- or p-hydroxybenzaldehyde, p-methoxybenzaldehyde, etc.

Preferred aldehyde stabilizers include formaldehyde, paraformaldehyde, N-formyl piperidine and 3-methoxy-4-hydroxybenzaldehyde (especially paraformaldehyde).

The hereinbefore described aldehyde stabilizer is employed in the practice of the invention in a "stabilizing amount", which term is defined hereinbefore. Advantageously, such stabilizer is employed in an amount sufficient to reduce by at least about 20 percent (preferably by at least about 30 percent and most preferably by at least about 40 percent) the amount of antimicrobial compound which decomposes during about 15 days (preferably about 30 days) of storage at 50° C. Such decomposition reduction is, of course, relative to that which occurs under the same conditions in the absence of the aforementioned stabilizer. In quantitative terms, the amount of stabilizer needed to achieve the desired degree of stabilization can vary depending upon the remainder of the composition (i.e., the identity and concentration of the other ingredients in the particular composition involved) and upon the particular stabilizer employed. However, as a general rule the stabilizer constitutes between about 0.05 and about 10, preferably between about 0.1 and about 5, most preferably between about 0.5 and about 2, percent by weight of the total composition.

In addition to the hereinbefore defined ingredients, the aqueous antimicrobial composition of the invention can optionally contain other ingredients. Such optional ingredients can be inert in the sense that they neither inhibit nor accelerate decomposition of the antimicrobial compound. Alternatively, such optional ingredients can themselves be stabilizers for the halogenated amide antimicrobial. Thus, for example, the stabilized aqueous antimicrobial composition of the invention can, in addition to the aforementioned aldehyde stabilizer, further comprise other compounds which are stabilizers in their own right as disclosed in commonly owned applications filed even date herewith. Such optional additional stabilizers include acids or anhydrides (e.g., acetic acid, ethylenediaminetetraacetic acid, succinic acid, succinic anhydride, glucolic acid, etc.) as disclosed by George A. Burk; carbamoyl or sulfamoyl compounds (e.g., N-methyl urea, N,N-diethyl urea, biuret, sulfamide, oxamide, N,N-dimethylformamide, caprolactam, N-methyl-2-pyrrolidone, dimethylhydantoin, succinimide, etc.) as disclosed by George A. Burk and Charles E. Reineke; cyclic ethers (e.g., 1,4-dioxane, sym-trioxane, tetrahydrofuran, N-methyl morpholine, etc.) as disclosed by George A. Burk ad Charles A. Wilson; quaternary salts (e.g., methyl triphenyl phosphonium bromide, n-$C_{12}$-$C_{18}$ alkyl dimethyl benzyl ammonium chloride, etc.) as disclosed by George A. Burk; and azine or nitrile compounds (e.g., cyanuric acid, 2-chloro-4,6-bis-(ethylamino)-s-triazine, cyanoguanidine, succinonitrile, etc.) as disclosed by George A. Burk. The amount of such additional stabilizer which is desirably employed varies depending upon a number of factors, such as the identity and amounts of the specific ingredients involved. However, when such additional stabilizer is employed, it is generally used in an amount between about 0.1 and about 2 (preferably between about 0.2 and about 1) percent by weight based upon the total weight of the antimicrobial composition.

The order of combination of the hereinbefore described ingredients is not critical to the obtention of a decreased decomposition rate relative to that obtained with the corresponding non-stabilized composition. However, in order to avoid excessive amounts of decomposition prior to stabilization, it is generally desirable to avoid prolonged exposure of the antimicrobial compound to the water in the composition prior to addition of the stabilizer thereto. Similarly, it is generally desirable, in order to retain optimum antimicrobial activity, to prepare, store, transport and handle the stabilized compositions of the invention at the lowest practicable temperature (normally ambient temperature) and at a pH between about 2 and about 5 (preferably between about 3 and about 4).

As has been noted, the hereinbefore described stabilizers have been found to reduce the halogenated amide antimicrobial decomposition rate in a mixture of an organic solvent and water. A particularly beneficial result of such phenomenon is that suitably stable halogenated amide antimicrobial compositions can be prepared directly from a mixture of the antimicrobial and the aqueous reaction medium in which it was prepared. Specifically, separation of the halogenated amide antimicrobial from its aqueous reaction medium is conveniently eliminated by incorporating such reaction medium into the antimicrobial composition and by counteracting the otherwise adverse impact of the water in such reaction medium by adding the aforementioned aldehyde stabilizer.

Thus, in one aspect this invention is a process for preparing the aforementioned stabilized aqueous antimicrobial compositions, which process comprises the steps of (a) preparing the halogenated amide antimicrobial by the acid catalyzed reaction of the corresponding non-halogenated amide with halogen in aqueous solution; (b) dissolving the resulting aqueous reaction mixture in the hereinbefore described water miscible organic solvent; and (c) adding to the reaction mixture, or to the water soluble organic solvent solution thereof, a stabilizing amount of the aforementioned aldehyde stabilizer. Typically, the aforementioned process also comprises an additional step in which the pH of the reaction mixture, the organic solvent solution, or the stabilized organic solvent solution is adjusted such that the pH of the antimicrobial composition if from about 2 to about 5, preferably from about 3 to about 4. Preferably, such pH adjustment step is performed following preparation of the halogenated amide and prior to dissolution of the reaction mixture in the organic solvent. In such instance, adjustment of the pH to a value of from about 5 to about 7 (preferably from about 5.5 to about 6.5) typically provides the antimicrobial composition with a pH within the desired range following the dissolution step.

The particular reagent employed to adjust the pH in the aforementioned pH adjustment step is not particularly critical. However, as a general rule, alkali metal or alkaline earth metal carbonates or bicarbonates (especially sodium carbonate) are advantageously employed.

The preparation of the halogenated amide antimicrobial (i.e., step (a) above) can be accomplished in any convenient conventional manner. Thus, for example, the halogenated amide antimicrobial can be prepared by the acid catalyzed reaction of the corresponding non-halogenated amide (e.g., cyanoacetamide, malonic diamide, and N-substituted derivatives thereof) with halogen (especially bromine) in aqueous solution, preferably at a temperature of less than about 40° C. and preferably at a hydrogen halide (which is a reaction by-product) concentration of less than about 20 weight percent on a total weight basis.

Preferably, however, the initial step of such process is performed pursuant to the improved procedure which is disclosed by U.S. Pat. No. 3,751,444. In such preferred process for preparing the halogenated amide antimicrobial, the improved aspect comprises introducing a water-soluble bromate into the aqueous reaction medium. Further details relating to the practice of such preferred initial step are found in U.S. Pat. No. 3,751,444, the disclosure of which is hereby incorporated by reference.

After the halogenated amide antimicrobial has been prepared in the aforementioned manner, the resulting reaction mixture is dissolved in the hereinbefore described organic sovlent. Such dissolution step is performed either before or after addition of the stabilizer and without isolation of the halogenated amide antimicrobial from the aqueous reaction medium. Any of the hereinbefore described water miscible organic solvents can be suitably employed in such dissolution step. However, as has been noted, the presence in such solvent of salts of organic acid and/or glycols having a molecular weight of less than about 70 has been observed to deleteriously affect the stability of the halogenated amide antimicrobial. Accordingly, it is preferable (in order to obtain optimum stability in the resulting compositions of the instant process) to employ an organic solvent of the hereinbefore described type which is substantially free both of salts of organic acids and of glycols having molecular weights of less than about 70 grams per mole.

In the aforementioned process, it is generally desirable to avoid prolonged exposure of the halogenated amide antimicrobial to the aqueous reaction medium in the absence of the stabilizer in order to prevent excessive loss (i.e., decomposition) of the halogenated amide product prior to stabilization. In addition, the pH adjustment step is also desirably accomplished without prolonged delay since the decomposition rate of the halogenated amide antimicrobial is generally pH dependent and since such decomposition rate is typically minimized within the indicated pH range. In addition, since the rate of decomposition of the halogenated amide antimicrobial increases with increased temperature, it is preferable to conduct the aforementioned individual process steps (and to store, transport and handle the resulting aqueous antimicrobial compositions) at ambient temperature (e.g., from about 20° to about 25° C.) or less in order to avoid excessive decomposition of the antimicrobial during such operations.

Naturally, in the practice of the aforementioned process, other ingredients such as those described hereinbefore, can be added to the aqueous composition either during or after its preparation pursuant to such process.

The practice of the instant invention is further illustrated by the following examples. In such examples all weight percentages are on a total weight basis unless otherwise indicated. The polyethylene glycol 200 employed in such examples is a commercial grade mixture of polyethylene glycols having a weight average molecular weight of about 200 and commercially available as Polyglycol E-200 from The Dow Chemical Company.

tested is then calculated on the basis of the amount of elemental iodine liberated thereby.

It should be noted that since certain of the intermediate decomposition products of DBNPA are also oxidizing agents, the indicated test method does not, strictly speaking, provide an exact measure of DBNPA content. However, such test method does provide a measure of the amount of DBNPA which has completely decomposed to the ultimate non-oxidizing species and thus provides a relative measure of the stability of the DBNPA compositions tested.

TABLE I

| | DBNPA CONTENTS AFTER VARIOUS STORAGE PERIODS at 50° C. | | | | | | | |
|---|---|---|---|---|---|---|---|---|
| | Composition[1] | | | | Initial | DBNPA Content After the | | |
| Example | | | Stabilizer | | DBNPA | Indicated Storage Period at 50° C.[1] | | |
| Number | P.E.G. 200 | Water | Type | Amount | Content | 15 Days | 25 Days | 36 Days |
| 1 | 47% | 47% | Formaldehyde | 0.7% | 5.0% | 4.2% | 4.0% | 3.75% |
| Control 1* | 95% | None | None | None | 5.0% | 4.8% | 4.6% | 4.3 % |
| Control 2* | 47.5% | 47.5% | None | None | 5.0% | 3.9% | 3.7% | 3.2 % |

*Not an example of the invention.
[1]The indicated percentages are in weight percent on a total weight basis.

EXAMPLE 1

Formaldehyde Stabilization of a Composition Comprising 2,2-dibromo-3-nitrilopropionamide, Polyethylene Glycol 200 and Water These experiments illustrate the increased rate of 2,2-dibromo-3-nitrilopropionamide (DBNPA) decomposition in the presence of water. The stabilizing effect of formaldehyde upon aqueous DBNPA compositions is also illustrated.

EXAMPLE 1

A 5 g portion of 2,2-dibromo-3-nitrilopropionamide (DBNPA) is placed in a 2 oz. amber bottle. To this is added 47 g of polyethylene glycol 200 (P.E.G. 200), 47 g of water and 2 g of an aqueous formaldehyde solution containing 36 weight percent formaldehyde.

Anhydrous Control (i.e., Control 1)

In a second 2 oz. amber bottle is placed 5 g of DBNPA and 95 g of P.E.G. 200.

Aqueous Control (i.e., Control 2)

In a third 2 oz. amber bottle is placed 5 g of DBNPA, 47.5 g of P.E.G. 200 and 47.5 g of water.

The contents of each of the three bottles are mixed until all of the ingredients are dissolved. The dissolution is accompanied by a temperature rise of about 5° C. After the heat of dissolution has dissipated, the initial DBNPA content is verified by iodometry. The bottles are then closed with a polyethylene lined cap and placed in a constant temperature oven at 50° C. for accelerated decomposition testing. The samples are removed periodically and the extent of DBNPA decomposition is determined by iodometry. The results of the accelerated decomposition testing are presented in Table I below.

In this example (and in the subsequent examples), the relative DBNPA content of the various antimicrobial compositions is determined by iodometry. In such test method, an excess of potassium iodide (KI) is added to the antimicrobial composition and the amount of elemental iodine which has been liberated from the KI (via oxidation of the KI by the DBNPA) is determined by titration with a standard solution of sodium thiosulfate. The amount of DBNPA present in the composition Comparison of Controls 1 and 2 illustrates the adverse effect of water upon the stability of DBNPA. For example, under aqueous conditions (i.e., Control 2) 36 percent of the DBNPA which was originally present decomposes during 36 days at 50° C., i.e., [(5.0-3.2)÷5.0]×100%. In contrast, the composition of Control 1 (i.e., substantially anhydrous) suffers a loss of only 14 percent of the DBNPA originally present) over the same time period at 50° C., i.e., [(5.0-4.3)÷5.0]×100%. Similar differences in DBNPA decomposition between Control 2 and Control 1 are reflected at the shorter test intervals.

The stabilizing effect of formaldehyde in the aqueous composition is observed by comparing Example 1 with Control 2. Such comparison shows that the stabilized aqueous composition of Example 1 exhibits substantially more retained DBNPA after each storage interval than does the non-stabilized aqueous composition of Control 2. In particular, it is noted that the stabilized aqueous composition of Example 1 exhibits about 30 percent less DBNPA decomposition after 36 days at 50° C. than does the corresponding non-stabilized aqueous composition of Control 2.

EXAMPLE 2

Aqueous Solution of DBNPA in P.E.G. 200 Stabilized with Vanillin

Pursuant to the procedure of Example 1 a solution containing 5 percent by weight DBNPA, 47 percent by weight P.E.G. 200, 47 percent by weight water, and 1 percent by weight vanillin (i.e., 3-methoxy-4-hydroxybenzaldehyde) is prepared, thereby forming the composition of Example 2. In addition, an aqueous control solution containing 5 weight percent DBNPA and 95 weight percent of a 50:50 (by weight) mixture of water and P.E.G. 200 is prepared for comparison.

Both solutions are then stored at 50° C. for 9 days and at the end of that period the DBNPA content of each of the solutions is determined by iodometry.

After 9 days of storage at 50° C. the stabilized aqueous formulation of Example 2 contains 4.5 weight percent DBNPA on a total weight basis; representing decomposition of one-tenth of the DBNPA initially present. After the same time period at 50° C., the non-stabilized aqueous control contains 4.35 weight percent DBNPA on a total weight basis; representing decomposition of 13 hundredths of the DBNPA initially. Accordingly, it is found that the stabilized aqueous composition of Example 2 exhibits about 23 percent (i.e., $[(0.13-0.10) \div 0.13] \times 100\%$) less DBNPA decomposition, during 9 days at 50° C. than does the corresponding non-stabilized aqueous composition under the same test conditions. The stabilizing effect of vanillin is thus readily apparent.

EXAMPLE 3

Aqueous Solution of DBNPA in P.E.G. 200 Stabilized with N-formyl Piperidine

Example 2 is repeated using N-formyl piperidine as a stabilizer in place of vanillin and a corresponding non-stabilized aqueous control is prepared for comparison. Both solutions are stored at 50° C. and samples are periodically taken from each solution for determination of DBNPA content via iodometry. The results are presented below:

|  | Percentage of the Original DBNPA Content Retained After the Indicated Storage Period at 50° C. | | |
|---|---|---|---|
|  | 10 Days | 20 Days | 34 Days |
| Example 3 | 97% | 93% | 85% |
| Non-stabilized Aqueous Control* | 89% | 74% | 66% |

*Not an example of the invention.

As is apparent from the foregoing results, the stabilized aqueous composition of Example 3 retains substantially more of its initial DBNPA content after each of the storage periods than does its non-stabilized aqueous counterpart.

EXAMPLE 4

Aqueous Solution of DBNPA in P.E.G. 200 Prepared Directly from the Aqueous DBNPA Reaction Medium and Stabilized with Paraformaldehyde A 26.0 g quantity (i.e., 0.3 mole) of commercial cyanoacetamide is dissolved in 95 ml of water and is then reacted with a 48 g portion (i.e., 0.3 mole) of bromine for half an hour at 22°-26° C. Thereafter, a 15.1 g portion of NaBrO$_3$ (in the form of a concentrated aqueous solution thereof) is slowly added to the reaction mixture over a 1½ hour period while continuing the reaction at 22°-26° C. An additional 2.0 g portion of bromine is then added and the reaction is continued for an additional 2-hour period.

The pH of the resulting reaction mixture is then adjusted to 6.0 with Na$_2$CO$_3$ and a 180 gram portion of polyethylene glycol 200 is added to dissolve the reaction mixture. The resultant solution has a pH of 3.5 and contains 19.3 weight percent DBNPA as determined by iodometric titration; representing a 98 percent yield of DBNPA.

One portion of the resulting solution is stabilized with 1 weight percent paraformaldehyde (thereby forming the composition of Example 4) and is analyzed (by iodometric titration) for retained DBNPA content after various storage intervals at 50° C.

A second portion of the resulting reaction mixture solution is stored, without stabilization, at 50° C. and analyzed for retained DBNPA in the same fashion for comparison. The results for both compositions are summarized below.

|  | Stabilizer | DBNPA Content After the Indicated Period at 50° C. | |
|---|---|---|---|
|  |  | 9 Days | 24 Days |
| Example 4 | 1 wt % paraformaldehyde | 18.5% | 17.0% |
| Non-stabilized Aqueous Control* | None | 17.9% | 14.6% |

*Not an example of the invention.

The foregoing results show that the stabilized aqueous composition of Example 4 exhibits significantly higher DBNPA content that does the corresponding non-stabilized aqueous control after both test intervals. In particular, it is noted that, after 24 days at 50° C., the stabilized composition has suffered 51 percent less DBNPA decomposition (i.e., $[(17.0-14.6) \div (19.3-14.6)] \times 100\%$) than has the corresponding non-stabilized aqueous control.

While the practice of the invention has been illustrated with reference to particular embodiments and examples, it should be understood that such embodiments and examples are not intended to limit the scope of the instantly claimed invention.

What is claimed is:

1. An aqueous antimicrobial composition having a pH of from about 2 to about 5 and comprising:
   (a) an alpha-halogenated amide antimicrobial compound of the formula:

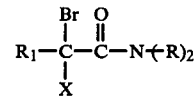

wherein:
   X is hydrogen, halogen or a cyano radical;
   each R group is independently hydrogen, a monovalent saturated hydrocarbon radical or an inertly substituted monovalent saturated hydrocarbon radical or the two R groups are jointly a divalent saturated hydrocarbon radical or an inertly substituted divalent hydrocarbon radical which, taken with the adjacent nitrogen atom, forms a heterocyclic ring having from 4 to about 10 ring members; and
   R$_1$ is a cyano radical or an amido radical of the formula:

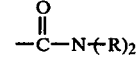

wherein R is as hereinbefore defined;
   (b) a water-miscible organic solvent in an amount sufficient to dissolve the halogenated amide antimicrobial, said water-miscible organic solvent being selected from normally liquid, polyalkylene glycols of the ethylene, trimethylene or tetramethylene series and the mono- or di-saturated hydrocarbyl ethers thereof;
   (c) water; and
   (d) a stabilizing amount of an aldehyde stabilizer selected from the group consisting of saturated aliphatic aldehydes, saturated alicyclic aldehydes and carbocyclic aromatic aldehydes, said stabilizing amount being an amount of the stabilizer sufficient to measurably reduce the decomposition rate of the halogenated amide antimicrobial in the aqueous antimicrobial composition.

2. The composition of claim 1 wherein the polyalkylene glycol or ether thereof has a weight average molecular weight of from about 75 to about 1000.

3. The composition of claim 1 wherein, in the antimicrobial compound:
X is hydrogen, chlorine or bromine;
each R group is independently hydrogen, a monovalent saturated hydrocarbon radical or an inertly substituted monovalent saturated hydrocarbon radical; and
$R_1$ is a cyano radical.

4. The composition of claim 1 wherein, in the antimicrobial compound:
X is hydrogen, chlorine or bromine and $R_1$ is a cyano radical.

5. The composition of claim 1 wherein the antimicrobial compound is 2,2-dibromo-3-nitrilopropionamide.

6. The composition of claim 1 wherein the aldehyde stabilizer is formaldehyde, paraformaldehyde, N-formyl piperidine or 3-methoxy-4-hydroxybenzaldehyde.

7. The composition of claim 6 wherein the water-soluble organic solvent is polyethylene glycol, having a weight average molecular weight of about 200; the anti-microbial compound is 2,2-dibromo-3-nitrilopropionamide and the pH of the aqueous antimicrobial composition is from about 3 to about 4.

8. The composition of claim 1 wherein the aldehyde stabilizer is paraformaldehyde.

9. The composition of claim 1 wherein:
(a) the antimicrobial compound constitutes from about 1 to about 25 weight percent of the total composition;
(b) the water constitutes from about 20 to about 60 weight percent of the total composition;
(c) the water-miscible organic solvent constitutes from about 25 to about 75 weight percent of the total composition; and
(d) the aldehyde stabilizer constitutes from about 0.1 to about 5 weight percent of the total composition.

10. A process for preparing the aqueous antimicrobial composition of claim 1 which process comprises the steps of:
(a) preparing the alpha-halogenated amide antimicrobial by the acid catalyzed reaction of the corresponding nonhalogenated amide with halogen in aqueous solution, at a temperature of less than about 40° C. and in the presence of hydrogen halide at a concentration which is less than 20 weight on a total weight basis but which is sufficient to catalyze the reaction;
(b) dissolving the resulting aqueous reaction mixture in the water-miscible organic solvent;
(c) adding to the reaction mixture of step (a), or to the water-miscible organic solvent solution of step (b), a stabilizing amount of the aldehyde stabilizer; and
(d) adjusting the pH of the product of step (a), (b) or (c) such that the aqueous antimicrobial composition has a pH of from about 2 to about 5.

11. The process of claim 10 in which the pH adjustment is such that the aqueous antimicrobial composition has a pH of from about 3 to about 4.

12. The process of claim 10 wherein the halogenated amide antimicrobial is 2,2-dibromo-3-nitrilopropionamide, the nonhalogenated amide is cyanoacetamide and the halogen is bromine; the water-miscible organic solvent is polyethylene glycol, or a lower alkyl ether thereof, having a weight average molecular weight of about 200; and the aldehyde stabilizer is paraformaldehyde.

13. The process of claim 10 wherein a water-soluble bromate is introduced to the aqueous reaction medium during preparation of the halogenated amide antimicrobial; and the pH of the aqueous reaction mixture is adjusted to a value of from about 5 to about 7 by the addition of an alkali metal, or an alkaline earth metal, carbonate or bicarbonate to such reaction mixture following the preparation of the halogenated amide and prior to the dissolution of the reaction mixture in the organic solvent.

14. An aqueous antimicrobial composition having a pH of from about 2 to about 5 and comprising, based upon the total weight of such composition:
(a) from about 1 to about 25 weight percent of a halogenated amide antimicrobial of the formula:

$$N\equiv C-\underset{\underset{X}{|}}{\overset{\overset{Br}{|}}{C}}-\overset{\overset{O}{\|}}{C}-N\diagup_{R}^{R}$$

wherein X is hydrogen, chlorine or bromine and each R is independently hydrogen, an alkyl group of from 1 to about 6 carbon atoms or phenyl;
(b) from about 5 to about 90 weight percent of water;
(c) from about 5 to about 90 weight percent of a water-miscible organic solvent which is selected from the group consisting of polyethylene glycols, trimethylene glycols, tetramethylene glycols and the mono- and di- phenyl or $C_1$ to about $C_6$ alkyl ethers thereof and which has a weight average molecular weight of from about 75 to about 1000; and
(d) a stabilizing amount, in the range of from about 0.05 to about 10 weight percent, of an aldehyde stabilizer selected from the group consisting of saturated aliphatic aldehydes, saturated alicyclic aldehydes and carbocyclic aromatic aldehydes.

15. The composition of claim 14 wherein the halogenated amide antimicrobial is 2,2-dibromo-3-nitrilopropionamide.

16. The composition of claim 15 wherein the water-miscible organic solvent is polyethylene glycol having a weight average molecular weight of from about 175 to about 250.

17. The composition of claim 15 wherein the water-miscible organic solvent is polyethylene glycol 200.

18. The composition of claim 16 wherein the aldehyde stabilizer is formaldehyde, paraformaldehyde, N-formyl piperidine or 3-methoxy-4-hydroxybenzaldehyde.

19. A process for preparing the aqueous antimicrobial composition of claim 18 which process comprises the steps of:
(a) preparing the 2,2-dibromo-3-nitrilopropionamide by the reaction of cyanoacetamide with bromine in aqueous solution (1) at a temperature of less than about 40° C., (2) in the presence of HBr at a concentration which is less than about 20 weight percent on a total weight basis but which is sufficient to catalyze the reaction and (3) in the presence of an alkali metal or an alakaline earth metal bromate;

(b) dissolving the resulting aqueous reaction mixture in the polyethylene glycol having a weight average molecular weight of from about 175 to about 250;

(c) adding to the reaction mixture of step (a) or to the solution thereof of step (b) a stabilizing amount of the aldehyde stabilizer; and (d) adjusting the pH of the product of step (a), (b) or (c) such that the aqueous antimicrobial composition has a pH of from about 2 to about 5.

* * * * *

UNITED STATES PATENT AND TRADEMARK OFFICE
CERTIFICATE OF CORRECTION

PATENT NO. : 4,163,798                                        Page 1 of 2

DATED : August 7, 1979

INVENTOR(S) : George A. Burk; Charles A. Wilson; Charles E. Reineke

It is certified that error appears in the above-identified patent and that said Letters Patent are hereby corrected as shown below:

Column 3, line 60, delete "mino-" and insert --mono- --.

Column 3, line 62, delete "amino" and insert --amido--.

Column 3, line 65, delete "bromomalonic" and insert --chloro-2-bromomalonic--.

Column 4, line 34, delete "crobal" and insert --crobial--.

Column 4, line 37, delete "abou" and insert --about--.

Column 6, line 18, delete "ybenaldehyde" and insert --ybenzaldehyde--.

Column 6, line 60, delete "glucolic" and insert --glycolic--.

UNITED STATES PATENT AND TRADEMARK OFFICE
CERTIFICATE OF CORRECTION

PATENT NO. : 4,163,798
DATED : August 7, 1979
INVENTOR(S) : George A. Burk; Charles A. Wilson; Charles E. Reineke It is certified that error appears in the above-identified patent and that said Letters Patent are hereby corrected as shown below:

Column 6, line 68, delete "ad" and insert --and--.

Column 7, line 60, delete "if" and insert --is--.

Column 8, line 32, delete "sovlent" and insert --solvent--.

Column 12, line 15, delete "that" and insert --than--.

Column 14, line 68, delete "alakaline" and insert --alkaline--.

Signed and Sealed this

Thirteenth Day of November 1979

[SEAL]

Attest:

RUTH C. MASON
Attesting Officer

LUTRELLE F. PARKER
Acting Commissioner of Patents and Trademarks